United States Patent [19]

Fried

[11] Patent Number: 5,155,280

[45] Date of Patent: Oct. 13, 1992

[54] PROCESS FOR THE OXIDATION OF ALCOHOLS TO ALDEHYDES

[75] Inventor: Herbert E. Fried, Houston, Tex.

[73] Assignee: Shell Oil Company, Houston, Tex.

[21] Appl. No.: 759,070

[22] Filed: Sep. 30, 1991

[51] Int. Cl.$^5$ .................... C07C 45/38; C07C 45/39
[52] U.S. Cl. .................... 568/471; 568/426; 568/436; 568/442; 568/449; 568/470
[58] Field of Search ............ 568/426, 449, 470, 471, 568/472, 485, 486, 497, 436, 442, 455

[56] References Cited

U.S. PATENT DOCUMENTS 4,620,033 10/1986 Isshiki et al. .................... 562/519

FOREIGN PATENT DOCUMENTS 5096516 11/1986 Japan .

OTHER PUBLICATIONS

Miyazawa et al., "Oxidation of Benzyl Alcohol with Iron(III) Using Polymers Containing Nitroxyl Radical Structure as a Mediator", J. Polym. Sci., Polym. Chem. Ed., 23(9), 1985, pp. 2487–2494.
Grigor'ev et al., "Participation of Nitroxyl Radical in the Oxidation of Aldehyde and Alcohol Groups in 3-Imidazolin-1-oxyls", Izc. Akad. Nauk SSSR, Ser. Khim., (1), 1978, pp. 208–210.
Miyazawa et al., "Oxidation of Benzyl Alcohol with Copper(II) Mediated by a Polymeric Oxoaminium Salt", J. Mol. Catal., 49(1), 1988, 131–134.
Ganem et al., "Biological Spin Labels as Organic Reagents. Oxidation of Alcohols to Carbonyl Compounds Using Nitroxyls", J. Org. Chem. 40(13), 1975, pp. 1998–2000.
Miyazawa et al., "Oxidation of Benzyl Alcohol by Iron(III) Mediated by Nitroxyl Radical", J. Mol. Catal., 31(2), 1985, pp. 217–220.
Anelli et al., "Fast and Selective Oxidation of Primary Alcohols to Aldehydes or to Carboxylic Acids and of Secondary Alcohols to Ketones Mediated by Oxoammonium Salts Under Two-Phase Conditions", J. Org. Chem., 52 (12), pp. 2559–2562.
Inokuchi et al., "A Selective and Efficient Method for Alcohol Oxidations Mediated by N-Oxoammonium Salts in Combination with Sodium Bromite", J. Org. Chem., 1990, 55, pp. 462–466.
Organic Synthesis, vol. 69, p. 212 (1990).
Semmelhack et al., "Oxidation of Alcohols to Aldehydes with Oxygen and Cupric Ion, Mediated by Nitrosonium Ion", J. Am. Chem. Soc. 1984, 106, 3374–3376.
Yamaguchi et al., "Application of Redox System Based on Nitroxides to Organic Synthesis", Pure & Applied Chemistry, vol., 62(2), 1990, pp. 217–222.

Primary Examiner—Werren B. Lone
Attorney, Agent, or Firm—Pamela J. McCollough

[57] ABSTRACT

A process for the preparation of an aldehyde which comprises reacting the corresponding alkanol with a solubilized stable free radical nitroxide having the formula:

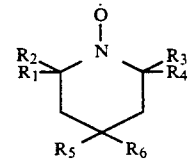

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, an alkali metal nitrosodisulfonate, a non-basic polar solvent and an oxidant, for about eight hours or less at a temperature in the range of from about 10° C. to about 20° C. and thereafter separating out the aldehyde.

15 Claims, No Drawings

PROCESS FOR THE OXIDATION OF ALCOHOLS TO ALDEHYDES

FIELD OF THE INVENTION

This invention relates to a process for the preparation of aldehydes by the oxidation of the corresponding alcohols in the presence of a stable free radical nitroxide, an alkali metal nitrosodisulfonate, a non-basic polar solvent and an oxidant.

BACKGROUND OF THE INVENTION

It is known to use nitroxyl radicals/oxoammonium salts in the oxidation of primary alcohols to produce aldehydes and acids and the oxidation of secondary alcohols to produce ketones (*Journal of Organic Chemistry*, vol. 52 (12), pp. 2559–2562 and *Journal of Organic Chemistry*, vol. 55, 1990, pp. 462–466).

It is reported in the open literature that primary aliphatic alcohols can be converted to aldehydes, but only in 30–40% yields in the presence of catalytic amounts of cuprous chloride, 2,2,6,6,-tetramethylpiperidine-1-oxyl, and atmoshperic oxygen (*Journal of American Chemical Society*, 1984, 106 pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217–222).

OBJECTS OF THE INVENTION

It is an object of this invention to produce aldehydes with high selectivities at moderate conversions from alkanols without producing large amounts of other products such as acids and esters.

It has been found that aldehydes can be produced with high selectivites and moderate conversions by using catalytic amounts of a stable free radical nitroxide, an alkali metal nitrosodisulfonate and an oxidant.

SUMMARY OF THE INVENTION

This invention relates to a process for the preparation of an aldehyde which comprises reacting the corresponding alkanol with a solubilized stable free radical nitroxide having the formula:

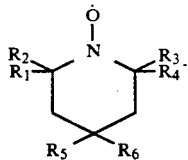

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, an alkali metal nitrosodisulfonate, a non-basic polar solvent and an oxidant at a temperature in the range of from about $-10°$ C. to about 20° C. for about eight hours or less, and thereafter separating out the aldehyde.

DESCRIPTION OF THE PREFERRED EMBODIMENTS

The present process converts alkanols to the corresponding aldehydes by contacting the alkanol with a solubilized stable free radical nitroxide, an alkali metal nitrosodisulfonate, a non-basic polar solvent and an oxidant, for about eight hours or less at a temperature in the range of from about $-10°$ C. to about 20° C.

The alkanol reactant suitably comprises one or more alkanols having a carbon number in the range of from about 1 to about 45. An alkanol consisting essentially of primary, mono-alkanols is preferred. Most preferably, the alkanol reactant consists essentially of one or more $C_6$ to $C_{30}$ primary mono-alkanols. Preference can also be expressed for alkanols having from 8 to about 20 carbon atoms, with $C_9$ to $C_{18}$ alkanols considered more preferred and $C_{11}$ to $C_{18}$ alkanols considered most preferred. As a general rule, the carbon chains of the alkanols may be of either branched or linear (straight-chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such alkanols as reactants in oxidation reactions is well recognized in the art. Examples of specific alkanols and of commercially available alkanols and alkanol mixtures within this class are also well known.

Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the presursor to a stable free radical from which the stable free radical may be produced in situ.

The stable free radical nitroxides, as used in the present process, are precursors to catalysts, i.e., oxoammonium salts, active for the oxidation of alkanols to the corresponding aldehydes. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

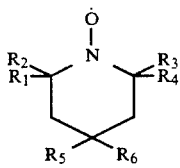

wherein each of $R_1$, $R_2$, $R_3$ and $R_4$ is an alkyl, aryl or heteroatom substituted alkyl group having 1 to about 15 carbon atoms, and no hydrogen is bound to the remaining valences on the carbon atoms bound to the nitrogen, and each of $R_5$ and $R_6$ is alkyl, hydrogen, aryl or a substituted heteroatom. As used herein, the term "alkyl" is meant to include cycloalkyl. The alkyl (or heteroatom substituted) groups $R_1$–$R_4$ may be the same or different, and preferably contain 1 to 15 carbon atoms. Preferably, $R_1$–$R_4$ are methyl, ethyl, or propyl groups. In addition to hydrogen, the heteroatom substituents may include, halogen, oxygen, nitrogen and the like. Preferably, one of $R_5$ and $R_6$ is hydrogen while the other is a substituted heteroatom which does not interfere with the reaction. Suitable substituted heteroatoms include, —OR,

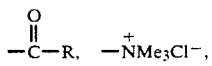

—O—SO$_3$H, —O—polymer and the like.

In a preferred embodiment, the nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

The alkali metal nitrosodisulfonate reactant may suitably be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate can be added to water prior to being added to the reaction mixture, although is typically added as a solid after all of the other reactants have been added. While not wishing to be bound by any particular theory, it is believed that the alkali metal nitrosodisulfonate decomposes under the reaction conditions, and one or more of these decomposition products appears, in the presence of an oxidant, to become an oxidant which is capable of oxidizing the nitroxide to an oxoammonium salt. It is believed that nitrogen oxides (NO$_x$) are generated in the reaction and are the active species.

The oxidants suitable for use in the instant invention are those compounds which are capable of oxidizing the stable free radical nitroxide to the oxoammonium salt. Suitable oxidants include oxygen or an oxygen-containing gas such as air. Whereas pure oxygen is preferred to accomplish the desired conversion, the oxygen can be diluted with an inert gas such as nitrogen, helium, argon, or other similar gas. While air can be used as the oxidant, the reaction rate is much slower. For purposes of increasing the reaction rate, higher O$_2$ pressures such as, for example, 1000 psi can be utilized. In a preferred embodiment, pure oxygen is used as the oxidant and it is bubbled into the reaction solution. In another embodiment, oxygen can be bubbled initially through the reaction solution in order to commence the reaction and then the flow of oxygen can be stopped without stopping the reaction.

The amounts and concentrations of the reactants utilized in the process of the instant invention can vary widely. The amount of stable free radical nitroxide is typically in the range of from about 1 mole percent to about 50 mole percent, preferably from about 5 mole percent to about 20 mole percent, basis the weight number of moles of the starting alkanol. Generally, the amount of an alkali metal nitrosodisulfonate utilized will be in the range of from about 1 mole percent to about 35 mole percent, preferably from about 10 mole percent to about 20 mole percent, basis the number of moles of starting alkanol.

The reaction in the instant invention is carried out utilizing a solubilized stable free radical nitroxide. The solvent utilized is a non-basic polar solvent, i.e., a solvent which does not form a strong complex with the oxoammonium ion, in which the alkanol is readily soluble. While the reaction will proceed if non polar solvents are utilized, the reaction times are so much slower that typically less than 10% conversions are obtained, even with extended reaction times. When basic polar solvents are utilized in the reaction, the reaction proceeds at an extremely slow rate and significant amounts of aldehydes are not produced. Non-basic polar solvents which are most suitable are those having dielectric constants less than about 20 and those solvents which are inert in the reaction. The solvent may be added to the reaction mixture or, alternatively, the nitroxide may be dissolved in the solvent prior to addition of the alkali metal nitrosodisulfonate to the reaction medium. The solvent is typically selected from the group consisting of with acetonitrile, dimethylsulfolane, nitroethane, and mixtures thereof, with acetonitrile being preferred. The amount of solvent utilized in the process is generally from about 20:1 to about 0.5:1, preferably from about 10:1 to about 5:1, basis the weight of the starting alkanol.

The process of the present invention is typically conducted under mild conditions, with good results being obtained using a temperature in the range of from about $-10°$ C. to about 20° C., preferably from about 0° C. to about 20° C. and more preferably from about 10° C. to about 15° C. Reaction pressures are not critical although higher pressures result in increased reaction rates. Pressures in the range of from about atmospheric pressure up to about 1000 psig can be employed with good results. The time of reaction required in order to obtain a high selectivity to aldehydes is typically about eight hours or less. The time in which the reaction proceeds to aldehydes will, however, be longer in the event that non polar solvents such as dichloromethane, carbon tetrachloride and heptane are used. The optimum times and temperatures for maximizing the selectivity to aldehydes can be readily determined by one skilled in the art with a minimal amount of routine experimentation.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of alkanol, 0.006 moles of the nitroxide, 0.0075 moles of an alkali metal nitrosodisulfonate which has been dissolved in water and solvent may be added to the reaction vessel, followed by bubbling an $O_2$ stream through the reaction mixture. Alternatively, the alkanol, the alkali metal nitrosodisulfonate and solvent may be added to the reaction vessel and allowed to reach equilibrium, followed by the dropwise or immediate addition of 10 mole percent of nitroxide which has been dissolved in a minimum amount of solvent. In a preferred embodiment, the reaction is carried out by adding the alkanol, the nitroxide, the solvent and the alkali metal nitrosodisulfonate together and then bubbling an oxidizing gas through the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such for example, as distillation.

Depending upon process conditions and the nitroxide used, the selectivity to aldehyde obtained by this invention can be greater than about 65%. The products produced by the instant process can be used in a variety of applications. For example, these products are typically used as or as intermediates in the preparation of esters, imides, acids, imines and amines.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

Illustrative Embodiments

EXAMPLE 1

6 Grams of 1-dodecanol, 1 gram of 2,2,6,6-tetramethyl-piperidine-1-oxyl, 50 milliliters of acetonitrile, 2 milliliters of water and 2 grams of potassium nitrosodisulfonate were charged to a 100 milliliter round bottomed flask. An $O_2$ stream was then bubbled through this mixture at atmospheric pressure. The reaction temperature was held at 10° C. over an 8 hour period. The results are presented in Table I.

EXAMPLE 2

6 Grams of 1-dodecanol, 1 gram of 2,2,6,6-tetramethylpiperidine-1-oxyl, 50 milliliters of acetonitrile, 2 milliliters of water and 1.0 grams of potassium nitrosodisulfonate were charged to a 100 milliliter round bottomed flask. An $O_2$ stream was then bubbled through this mixture at atmospheric pressure. The reaction temperature was held at 15° C. over a 4 hour period. The results are presented in Table I.

COMPARATIVE EXAMPLE A

Comparative Example A was carried out in a manner similar to Example 1 except that the reaction was run at 35° C. The results are presented in Table I.

COMPARATIVE EXAMPLE B

Comparative Example B was carried out in a manner similar to Example 1, except that the reaction was performed using heptane instead of acetonitrile and the reaction was held at 20° C. over a sixteen hour period. The results are presented in Table I.

As can be seen in Table I, reaction temperatures exceeding 20° C. result in the formation of carboxylic acids rather than the desired aldehydes. In addition, it can be seen that conversion to aldehydes is much slower in non polar solvents.

TABLE I

| Oxidation Of Alkanols to Aldehydes | | | | |
|---|---|---|---|---|
| | % Conversion | % Sel. Aldehydes | % Sel. Esters + Heavies | % Sel. Acids |
| Example 1 | 59 | 97 | 3 | 0 |
| Example 2 | 49 | 78 | 7 | 15 |
| Comparative Example A | 92 | 19 | 8 | 73 |
| Comparative Example B | 4.5 | 100 | 0 | 0 |

What is claimed is:

1. A process for the preparation of an aldehyde which comprises reacting the corresponding alkanol having a carbon number in the range of from about 1 to about 45 with a solubilized stable free radical nitroxide having the formula:

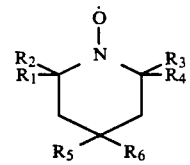

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, an alkali metal nitrosodisulfonate selected from the group consisting of potassium nitrosodisulfonate, sodium nitrosodisulfate and mixtures thereof, a non-basic polar solvent selected from the group consisting of acetonitrile, dimethylsulfolane, nitroethane and mixtures thereof, and an oxygen-containing gas, for about eight hours or less at a temperature in the range of from about 10° C. to about 20° C. and thereafter separating out the aldehyde.

2. The process of claim 1 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein said non-basic polar solvent is acetonitrile.

5. The process of claim 1 wherein said alkali metal nitrosodisulfonate is potassium nitrosodisulfonate.

6. The process of claim 1 wherein said alkanol is contacted with said solubilized stable free radical nitroxide and said alkali metal nitrosodisulfonate, followed by the addition thereto of said oxidant.

7. The process of claim 6 wherein the amount of solubilized stable free radical nitroxide is in the range of from about 1 mole percent to about 50 mole percent, basis the weight of the alkanol.

8. The process of claim 7 wherein the amount of said alkalimetal nitrosodisulfonate is in the range of from about 1 mole percent to about 35 mole percent, basis the number of moles of said alkanol.

9. The process of claim 1 wherein said alkanol is contacted with said alkali metal nitrosodisulfonate, followed by the addition thereto of said stable free radical nitroxide.

10. The process of claim 9 wherein the amount of solubilized stable free radical nitroxide is in the range of from about 1 mole percent to about 50 mole percent, basis the number of moles of said alkanol.

11. The process of claim 10 wherein the amount of said alkalimetal nitrosodisulfonate is in the range of from about 1 mole percent to about 35 mole percent, basis the number of moles of said alkanol.

12. The process of claim 1 wherein said oxygen-containing gas is selected from the group consisting of pure oxygen and air.

13. The process of claim 12 wherein said oxygen-containing gas is pure oxygen.

14. The process of claim 1 wherein said process is carried out at a temperature in the range of from about 0° C. to about 20° C. and at atmospheric pressure.

15. The process of claim 14 wherein said process is carried out at a temperature in the range of from about 10° C. to about 15° C. and at atmospheric pressure.

* * * * *

UNITED STATES PATENT AND TRADEMARK OFFICE
CERTIFICATE OF CORRECTION

PATENT NO. : 5,155,280
DATED : October 13, 1992
INVENTOR(S) : Herbert E. Fried

It is certified that error appears in the above-identified patent and that said Letters Patent is hereby corrected as shown below:

On the title page of the patent line "[21] Application No:" should be corrected to read:

[21] Appl. No.: 769,070

Signed and Sealed this

Twenty-sixth Day of October, 1993

Attest:

BRUCE LEHMAN

Attesting Officer

Commissioner of Patents and Trademarks